(12) United States Patent
Sumino et al.

(10) Patent No.: US 8,227,222 B2
(45) Date of Patent: Jul. 24, 2012

(54) METHOD AND APPARATUS FOR PRODUCING HYDROGEN AND MICROORGANISM-IMMOBILIZATION PELLETS USED IN THE SAME

(75) Inventors: Tatsuo Sumino, Tokyo (JP); Naoki Abe, Tokyo (JP); Hajime Ikuta, Tokyo (JP); Naomichi Mori, Tokyo (JP); Yutaka Mitani, Tokyo (JP); Yasuhiro Oki, Tokyo (JP)

(73) Assignees: Hitachi Plant Technologies, Ltd., Tokyo (JP); Sapporo Breweries, Ltd., Tokyo (JP)

( * ) Notice: Subject to any disclaimer, the term of this patent is extended or adjusted under 35 U.S.C. 154(b) by 305 days.

(21) Appl. No.: 12/532,941

(22) PCT Filed: Mar. 26, 2008

(86) PCT No.: PCT/JP2008/055689
§ 371 (c)(1),
(2), (4) Date: Sep. 24, 2009

(87) PCT Pub. No.: WO2008/120629
PCT Pub. Date: Oct. 9, 2008

(65) Prior Publication Data
US 2010/0136643 A1 Jun. 3, 2010

(30) Foreign Application Priority Data

Mar. 29, 2007 (JP) ................................ 2007-088663

(51) Int. Cl.
*C12P 5/02* (2006.01)
(52) U.S. Cl. ..................................................... 435/167
(58) Field of Classification Search .................. 435/167
See application file for complete search history.

(56) References Cited

FOREIGN PATENT DOCUMENTS

| JP | 7-31998 A | 2/1995 |
| JP | 2001-23677 A | 1/2001 |
| JP | 2001-229955 A | 8/2001 |
| JP | 2003-135088 A | 5/2003 |

OTHER PUBLICATIONS

Wu et al., process Biochemistry, 42(2), 279-284, Feb. 2007.*
Yokoi et al., "Hydrogen Production by Immobilized Cells of Aciduric Enterobacter aerogenes Strain HO-39", Journal of Fermentation and Bioengineering, 1997, vol. 83, No. 5, pp. 481-484.
Nikitina et al., Production of hydrogen by the thermophilic anaerobic bacterium clostridium thermosaccharolyticum, immobilized into polyvinyl alcohol cryogel., Mikrobiologiya, 1993, vol. 62, No. 3, pp. 477-488, Russian.
Ueno et al., "Operation of a two-stage fermentation process producing hydrogen and methane from organic waste", Environmental Science & Technology, Feb. 2007, vol. 41, No. 4, pp. 1413-1419.
Oki, et al., " Shokuhin Seizo Haikibutsu Karano Suiso/Methane Nidan Hakko Gijutsu", Kagaku Sochi, 2006, vol. 48, No. 7, pp. 42-46, Japanese.
Nishio et al, "Suiso Methane 2 Dan Hakko Gijutsu"., Kurin Enerugi 2005, vol. 14, No. 10, pp. 55-59, 76, Japanese.
Atsumi, et al "Shokuhin Seizo Haikibutsu no. Suiso Methane Nidan Hakko ni yoru Denki Netsu Energy Henkan ni Kansuru Jissho Kenkyo", "An empirical study of energy conversion from food processing-wastes by the hydrogen and methane two-stage anaerobic fermentation system", The Japan Society of Mechanical Engineers, 2004, Nendo Nenji Taikai Koen Ronbunshu (3), 2004, pp. 257-258, English Abstract. MM.
Deutsche Sammlung von Mikroorganismen and Zellkulturen GmbH (German Collection of Microorganisms and Cell Cultures).(online). (Retrieved on Apr. 17, 2008). Retrieved from the Internet: <URL:http://www.dsmz.de/microorganisms/html/bacteria.genus/thermoanaerobacterium.html>.
Edited by Chibata, Ichiro "Koteika Seitai Shokubai" Kodansha Ltd., 1986, 1st edition, pp. 145-147.
Chinese Office Action dated Sep. 21, 2011 issued in corresponding Chinese Application No. 200880010866.3.
David B. Levin et al.; Biohydrogen production prospects and limitations to practical application; International Journal of Hydrogen Energy: No. 29; pp. 173-185; 2004.

* cited by examiner

*Primary Examiner* — Maryam Monshipouri
(74) *Attorney, Agent, or Firm* — Birch, Stewart, Kolasch & Birch, LLP (57) ABSTRACT

The hydrogen-producing method of the an aspect of the present invention is a method for producing hydrogen in which hydrogen is produced from an organic matter using a microorganism, characterized by using pellets on which hydrogen-producing acid-resistant bacteria are entrapped and immobilized, producing hydrogen by bringing the pellets into contact and react with the organic matter in an environment of a pH of 4 to 6. The inventors of the present invention have obtained a finding that a hydrogen-producing bacteria are entrapped and immobilized, so that the optimum pH of the hydrogen-producing bacterium shifts to low range. The present invention is made based on the above finding and uses pellets on which the hydrogen-producing bacteria are entrapped and immobilized, so that the hydrogen-producing bacterium is activated at a low pH range of 4 to 6 to produce hydrogen. Therefore, the effects of contaminated bacteria that consume hydrogen are less, and the yield of hydrogen can be improved.

7 Claims, 5 Drawing Sheets

METHOD AND APPARATUS FOR PRODUCING HYDROGEN AND MICROORGANISM-IMMOBILIZATION PELLETS USED IN THE SAME

This application is a 371 of PCT/JP2008/055689, filed Mar. 16, 2008, which claims foreign priority to Japanese application 2007-088663, filed Mar. 29, 2007.

TECHNICAL FIELD

The present invention relates to a method and an apparatus for producing hydrogen and microorganism-immobilization pellets used in the same, and particularly relates to a method and an apparatus for producing hydrogen in which hydrogen is produced by hydrogen fermentation with a hydrogen-producing bacterium and microorganism-immobilization pellets used in the same.

BACKGROUND ART

With the increase in global warming, technologies for acquiring new energy without using fossil fuels have been developed, and the development of technologies for energy recovery from various biomass and renewable organic sources have been advanced in many areas. For example, hydrogen has attracted attention as a fuel that causes no environmental pollution and is currently mainly manufactured from fossil fuels. In order to acquire clean energy, the hydrogen fermentation by microorganisms using renewable organic resource as raw materials has been desired.

The renewable organic resources as raw materials used in the hydrogen fermentation include food waste, agricultural waste, and the like. Food waste includes food scraps in complex buildings (restaurants, hotels, offices, shops and the like), wastes of confectionery and bread in food factories, fruit processing remains, and the like. Using the above-mentioned renewable organic resources as raw materials, the hydrogen fermentation is performed using hydrogen-producing bacteria. As the hydrogen-producing bacteria, sludge in a solubilization tank at the pretreatment of methane fermentation is used as seed sludge. Obligate anaerobic bacteria and facultative anaerobic bacteria, which are hydrogen-producing bacteria, reside in this type of sludge. The Obligate anaerobic bacteria include *Clostridum butyricum* and *Clostridum beijerinckii*, and the facultative anaerobic bacteria include *Enterobacter aerogenes* and the like. The above-mentioned hydrogen-producing bacteria produce hydrogen via hydrogen fermentation of an organic matter as a substrate by a reaction with a retention time of 1 to 2 days.

As described above, an attempt to recover hydrogen from organic resources by hydrogen fermentation has been already reported. For example, Patent Documents 1 and 2 describe a method for recycling obtained hydrogen as an electrical energy. In addition, Patent Document 3 describes that the fermentation is performed under reduced pressure in order to lower the hydrogen partial pressure. Furthermore, Patent Document 4 describes a method and an apparatus for performing hydrogen fermentation using renewable organic waste as a raw material.

Patent Document 1: Japanese Patent Application Laid-Open No. 2001-23677
Patent Document 2: Japanese Patent Application Laid-Open No. 2001-229955
Patent Document 3: Japanese Patent Application Laid-Open No. 07-31998
Patent Document 4: Japanese Patent Application Laid-Open No. 2003-135088

DISCLOSURE OF THE INVENTION

Problems to be Solved by the Invention

However, the conventional methods and apparatus have a problem that the yield of hydrogen fermentation by hydrogen-producing bacteria is very low. For example, in a case where a hexose is used as a substrate, it is presumed from the metabolism system of it that up to 4 mol of hydrogen is theoretically produced per 1 mol of sugar. However, the yield of hydrogen fermentation ever reported is as low as 1 to 2 mol.

As one of the causes, it is considered that the yield may be decreased by the contamination with unwanted bacteria that consume hydrogen. In order to suppress the growth of unwanted bacteria, a method in which fermentation is conducted at low pH state is considered. However, the yield decreases at a pH of 6 or lower and the hydrogen fermentation is completely stopped at a pH of 5 or lower. Therefore, the hydrogen fermentation needs to be operated in an environment of a pH of 6 to 7 and has a problem that unwanted bacteria cannot be controlled.

As a method for solving the above problem, it is considered that a hydrogen-producing bacterium exhibiting a hydrogen fermentation activity at a pH of 6 or lower is used. However, enrichment culture of the above-described hydrogen-producing bacterium is very difficult and is unrealistic.

In view of the above background, a method for performing hydrogen fermentation in a high yield by maintaining the high activity of a hydrogen-producing bacterium at a pH of 4 to 6 is desired.

The present invention has been made in view of the above situation, and an object of the present invention is to provide a method and an apparatus capable of producing hydrogen in a high yield by performing hydrogen fermentation by a hydrogen-producing bacterium at a pH of 4 to 6 and microorganism-immobilization pellets used in the same.

Means for Solving the Problems

In order to achieve the above object, the first aspect of the present invention is a method for producing hydrogen in which hydrogen is produced from an organic matter using a microorganism, characterized by, using pellets on which hydrogen-producing acid-resistant bacteria are entrapped and immobilized, producing hydrogen by bringing the pellets into contact and react with the organic matter in an environment of a pH of 4 to 6.

The inventors of the present invention have obtained a finding that when hydrogen-producing bacteria are entrapped and immobilized, the optimum pH of the hydrogen-producing bacterium shifts to a lower range. The present invention is made based on the above finding and uses pellets on which hydrogen-producing bacteria are entrapped and immobilized, and as a result, hydrogen-producing bacteria are activated at a low pH range of 4 to 6 to produce hydrogen. Therefore, the effects of unwanted bacteria that consume hydrogen are less, and the yield of hydrogen can be improved.

In addition, as a method for entrapping and immobilizing hydrogen-producing bacteria, the method preferably comprises subjecting a liquid mixture prepared by mixing bacteria with an immobilizing material comprising prepolymer to polymerization, to entrap and immobilize bacteria on the internal of gel. As the prepolymer material, polyethylene glycol diacrylate and polyethylene glycol methacrylate are preferable, and derivatives thereof can be used. Also, the pellets are preferably entrapping pellets such as globular or cylindrical entrapping pellets, and entrapping pellets with many irregularities such as string-shaped entrapping pellets, and the contact efficiency and the hydrogen-producing rate are improved. In addition, the pellets preferably have a size equivalent to a globe with a size of 0.5 to 10 cm.

A second aspect of the present invention is, in the first aspect, characterized by using a strain identified by international deposit accession number FERM BP-10804 as hydrogen-producing bacteria, which is deposited to the International Patent Organism Depositary, National Institute of Advanced Industrial Science and Technology as *Thermoanaerobacterium* strain PEH8.

The inventors of the present invention have searched soil microorganisms, marine microorganisms, microorganisms in lakes and the like, separated a hydrogen-producing acid-resistant bacteria, *Thermoanaerobacterium* strain PEH8, and deposited it to the International Patent Organism Depositary, National Institute of Advanced Industrial Science and Technology as a strain identified by international deposit accession number FERM BP-10804 (date of international deposit: Mar. 26, 2007). The optimum pH of the above bacterium is in a range of 5.5 to 6.0, and the inventors of the present invention have found that when above bacteria are entrapped and immobilized, the optimum pH shifts to a range of 4 to 6. Therefore, hydrogen-producing bacteria of the second aspect are entrapped and immobilized and are used in an environment of a pH of 4 to 6, so that hydrogen can be obtained in a high yield.

Incidentally, scientific properties of the above bacteria (microorganism) are as follows:
  Gram stain: Positive
  Shape: Rod
  Oxygen requirement: Anaerobic (obligate).
A taxonomic position is,
  Genus: *Thermoanaerobacterium*
  Species: *thermosaccharolyticum*.

In order to achieve the above object, the third aspect of the present invention is an apparatus for producing hydrogen in which hydrogen is produced from an organic matter using a microorganism, characterized by comprising a hydrogen fermenter which produces hydrogen by charging pellets on which hydrogen-producing acid-resistant bacteria are entrapped and immobilized and bringing the pellets into contact and react with the organic matter and a pH control device which controls pH in the hydrogen fermenter to a range of 4 to 6. Hydrogen can be hereby produced in a high yield.

The fourth aspect of the present invention is, in the third aspect, characterized in that a methane fermenter for subjecting a waste liquid discharged from the hydrogen fermenter to methane fermentation is provided downstream of the hydrogen fermenter. According to the fourth aspect, a waste liquid after hydrogen fermentation is subjected to methane fermentation, so that an organic matter remained in the waste liquid is recovered as methane gas and can be utilized as energy.

The fifth aspect of the present invention is pellets suitable to be used in the first to fourth aspect. Since the optimum pH shifts to a range lower than the optimum pH before immobilization, hydrogen can be produced at a low pH range.

The sixth aspect of the present invention is, in the fifth aspect, characterized by using a strain identified by international deposit accession number FERM BP-10804 as hydrogen-producing bacteria, which is deposited to the International Patent Organism Depositary, National Institute of Advanced Industrial Science and Technology as *Thermoanaerobacterium* strain PEH8.

Advantage(s) of the Invention

According to the present invention, since hydrogen-producing acid-resistant bacteria are entrapped and immobilized and is used as pellets, hydrogen can be produced at a low pH region, and hydrogen can be obtained in a high yield without being contaminated with unwanted bacteria.

| Description of Symbols | |
|---|---|
| 10 | hydrogen-producing apparatus |
| 12 | hydrogen fermenter |
| 14 | pH control device |
| 16 | supply pipe |
| 18 | pellets |
| 20 | gas pipe |
| 22 | waste liquid pipe |
| 24 | adjuster supply pipe |
| 26 | on-off valve |
| 28 | pH meter |

BEST MODE FOR CARRYING OUT THE INVENTION

In accordance with the attached drawings, preferred embodiments of a method and an apparatus for producing hydrogen and microorganism-immobilization pellets used in the same of the present invention will be described hereinbelow.

Figure 1:
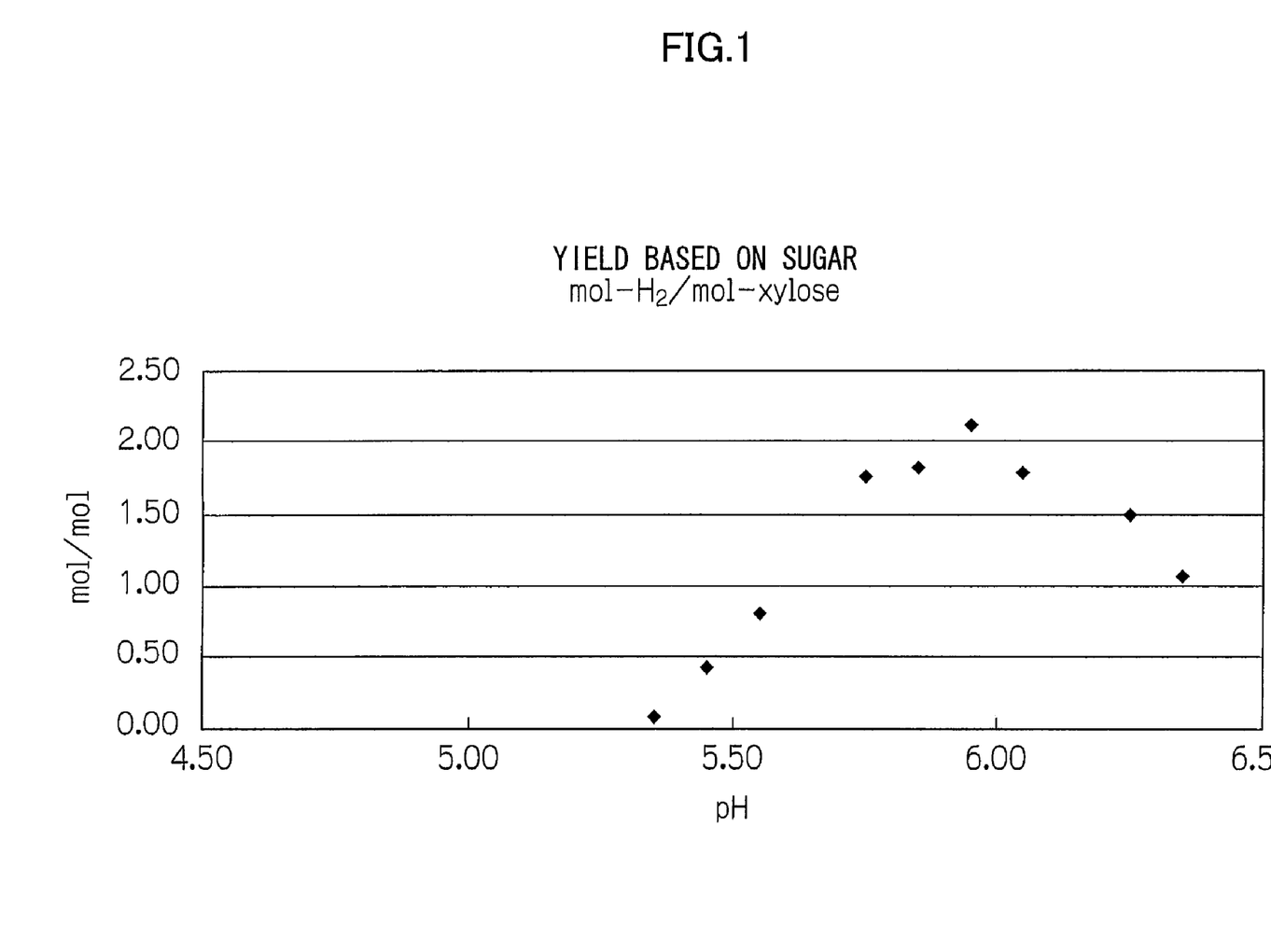
FIG. 1 is a graph showing the relationship between the activity of the hydrogen-producing bacteria and pH.
Figure 2:
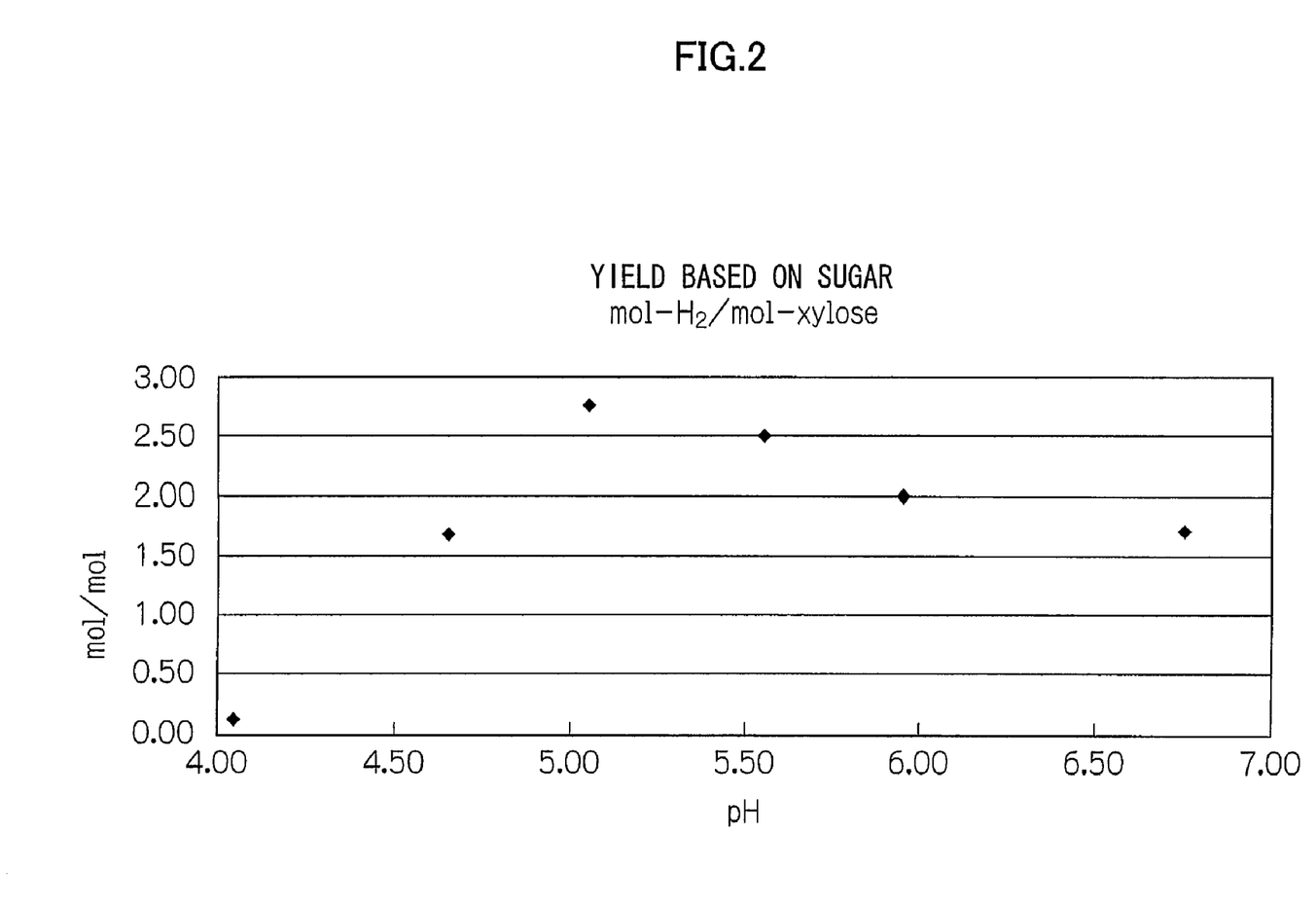
FIG. 2 is a graph showing the relationship between the activity of entrapped and immobilized hydrogen-producing bacteria and pH.

First, a data that is the basis of the present invention will be described. FIG. 1 shows the pH dependence of hydrogen-producing bacteria, *Thermoanaerobacterium* strain PEH8 (a strain identified by international deposit accession number FERM BP-10804, which is deposited to the International Patent Organism Depositary, National Institute of Advanced Industrial Science and Technology; hereinafter referred to as "*Thermoanaerobacterium* strain PEH8"), and FIG. 2 shows the pH dependence of pellets on which hydrogen-producing bacteria, *Thermoanaerobacterium* strain PEH8, is entrapped and immobilized.

Entrapping immobilization pellets were prepared as follows. Cells of *Thermoanaerobacterium* strain PEH8 were suspended to a urethane acrylate prepolymer solution, and potassium persulfate and NNN'N'-tetramethylethylenediamine were added thereto, so that the mixture was subjected to polymerization to give a gel entrapping the bacterium. The amount of each added is as follows.

$7\times10^7$ cells/ml solution of *Thermoanaerobacterium* strain PEH8 20%
  Urethane acrylate prepolymer 15%
  Sterile water 64.25%
  NNN'N'-tetramethylethylenediamine 0.5%
  Potassium persulfate 0.25%

The gel was formed into 3 mm square to give entrapping immobilization pellets. A 500-mL jar fermenter was charged with the resulting pellets in a volume of 10% and the continuous fermentations were performed at various pHs using the medium shown in Table 1. Table 2 shows the result. The operating conditions are at 55° C. and a medium feed rate of 100 to 300 mL/day.

TABLE 1

| Composition | Content |
| --- | --- |
| Xylose | 10 |
| Yeast Extract | 4.0 |
| MOPS | 2.5 |
| $K_2HPO_4$ | 0.91 |
| $NaH_2PO_4$ | 0.3 |
| $MgCl_2 \cdot 6H_2O$ | 0.2 |
| $CaCl_2 \cdot 2H_2O$ | 0.1 |
| $(NH_4)_2SO_4$ | 0.3 |
| $FeSO_4 \cdot 7H_2O$ | 0.02 |
| L-Cysteine Hydrochloride·$H_2O$ | 0.4 |
| Resazurin | 1.1 |
| Sterile Water | 1000 mL |

It is shown from FIG. 1 that the optimum pH of *Thermoanaerobacterium* strain PEH8 is from 5.5 to 6.5. Considering that the optimum pH of hydrogen-producing bacteria conventionally reported is from 6 to 6.5, it is shown that *Thermoanaerobacterium* strain PEH8 is acid-resistant bacterium exhibiting activity at low pH. In addition, as shown in FIG. 2, it is shown that above hydrogen-producing bacteria are immobilized, so that the optimum pH extends to a low range. More specifically, the range of the optimum pH extends to a pH of 4 to 6 and preferably a pH of 4.8 to 5.5. Therefore, pellets on which the above hydrogen-producing bacterium is entrapped and immobilized is used in an environment of a pH of 4 to 6 and preferably a pH of 4.8 to 5.5, so that hydrogen can be produced in a high yield.

Next, the comparison between the case where the above-described hydrogen-producing bacterium is used as entrapped and immobilized bacteria (pellets) and the case where the above-described hydrogen-producing bacterium is used as suspended bacteria will be explained on the basis of Table 2. Table 2 shows the result of yields obtained at various pHs using suspended bacteria and immobilized bacteria.

TABLE 2

| Method | pH | Yield (mol-$H_2$/mol-xylose) |
| --- | --- | --- |
| Suspended Bacterial Cells | 5 | 0 |
| Suspended Bacterial Cells | 5.5 | 0.8-1.0 |
| Suspended Bacterial Cells | 6.0 | 1.5-2.0 |
| Entrapped and Immobilized Bacterial Cells | 5 | 2.2-2.7 |
| Entrapped and Immobilized Bacterial Cells | 6.0 | 1.5-2.0 |

As it can be seen from Table 2, with bacteria in a suspended bacteria state, the activity rapidly decreases and the yield of hydrogen decreases to 1 or less at a pH of less than 6, and further, hydrogen is not obtained at all at a pH of 5 or less. On the other hand, with bacteria in an entrapped and immobilized state, the yield of hydrogen at a pH of 5 is higher than that at a pH of 6.

Hereinbelow, an apparatus for carrying out the present invention will be illustrated by examples.

Figure 3:
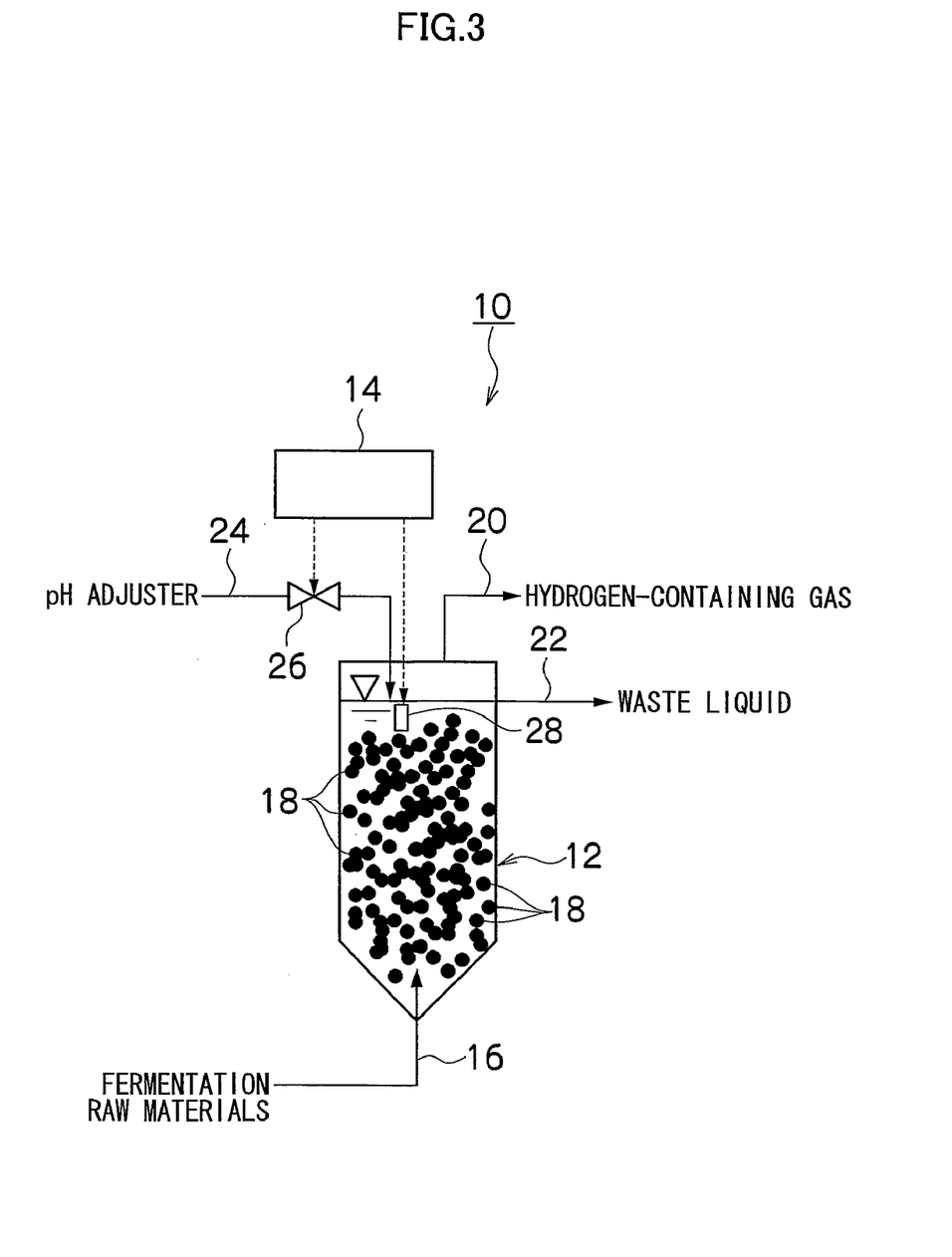
FIG. 3 is a diagram showing a hydrogen-producing apparatus to which the present invention is applied.

FIG. 3 schematically shows a constitution of a hydrogen-producing apparatus 10 of the present embodiment. As shown in the figure, the hydrogen-producing apparatus 10 is mainly constituted by a hydrogen fermenter 12 and a pH control device 14.

A supply pipe 16 is connected to the bottom part of the hydrogen fermenter 12, and fermentation raw materials are supplied to the hydrogen fermenter 12 via the supply pipe 16.

A plurality of pellets 18 are charged into the hydrogen fermenter 12. Each of the pellets 18 is one on which hydrogen-producing bacteria are entrapped and immobilized. As the hydrogen-producing bacterium, hydrogen-producing acid-resistant bacteria, for example, *Thermoanaerobacterium* strain PEH8, are used. As a method for producing the pellets 18, hydrogen-producing bacteria are mixed with an immobilizing material and the mixture is subjected to polymerization, so that the bacteria are entrapped and immobilized on the internal of a gel, to give the pellets 18. The immobilizing material is preferably a prepolymer material, and for example, polyethylene glycol diacrylate and polyethylene glycol methacrylate, and derivatives thereof are used. This is because, when a monomer such as acrylamide, methylenebisacrylamide, or triacrylformal is used as the immobilizing material, hydrogen generated in the internal of the pellets 18 accumulates in the internal of the pellets, and the pellets possibly blow out and burst. In addition, the immobilizing material is preferably a network gel having a molecular weight of 2000 to 9000. This is because, when the molecular weight is small, a shift range of the optimum pH is very small. The network gel having a molecular weight of 2000 to 9000 is used, so that the shift range of the optimum pH broadens, and a wide pH tolerance can be obtained. Also, the network gel having a molecular weight of 2000 to 9000 is used, so that the hydrogen generated in the internal of the pellets 18 is likely to permeate, and a blowout of the pellets 18 can be prevented.

When the pellets 18 is produced by a polymerization reaction, it is preferred that NNN'N'-tetramethylethylenediamine be added as a polymerization promotor. The agent is highly alkaline, and when a pH is elevated upon blending with the bacterium, the bacterium is killed. As the blending, NN'N'-tetramethylethylenediamine is added to a solution of urethane acrylate prepolymer plus bacteria, and thereafter, the polymerization initiator is added thereto, to polymerize the mixture. The pH upon adding NN'N'-tetramethylethylenediamine needs to be adjusted to 6 to 8 and preferably 6 to 7.

The pellets 18 preferably has a shape such as globular shape, rectangular shape, cylindrical shape, string shape or the like, and the pellets 18 preferably have a size equivalent to a globe with a size of 0.5 to 10 cm. The above-described pellets 18 are contacted with the fermentation raw materials within the hydrogen fermenter 12, so that hydrogen is produced.

A gas pipe 20 is connected to the upper part of the hydrogen fermenter 12. The hydrogen generated within the hydrogen fermenter 12 is transmitted to a downstream treatment apparatus (not shown in the figure) through the gas pipe 20 as a hydrogen-containing gas.

In addition, a waste liquid pipe 22 is connected to the upper side of the hydrogen fermenter 12, and a waste liquid in the hydrogen fermenter 12 is discharged outside via the waste liquid pipe 22. An end of the waste liquid pipe 22 is connected to a methane fermenter not shown in the figure, and an organic matter in the waste liquid is converted to methane gas in the methane fermenter.

On the other hand, a pH control device 14 is connected to an on-off valve 26 provided in an adjuster supply pipe 24. The adjuster supply pipe 24 is a line mainly for supplying an alkaline pH adjuster to the hydrogen fermenter 12, and one end of the adjuster supply pipe 24 is connected to the hydrogen fermenter 12, and the other end is connected to a pH adjuster tank (not shown in the figure). Therefore, the pH control device 14 opens and shuts the on-off valve 26, so that the pH adjuster is supplied to the hydrogen fermenter 12 via the adjuster supply pipe 24, and the pH in the hydrogen fermenter 12 is adjusted.

In addition, the pH control device 14 is connected to a pH meter 28 provided inside the hydrogen fermenter 12. Based on the pH value measured by the pH meter 28, the pH control device 14 controls the on-off valve 26 to supply the pH adjuster, and the internal of the hydrogen fermenter 12 is controlled to the given pH value. The given pH value in the present embodiment is a pH of 4 to 6 and preferably of 4.8 to 5.5.

According to the hydrogen-producing apparatus 10 constituted as described above, since hydrogen-producing bacteria are entrapped and immobilized as the pellets 18, the optimum pH shifts to low range, and the activity of hydrogen fermentation increases even at a low pH range of a pH of 4 to 6. Therefore, the internal of the hydrogen fermenter 12 is adjusted to a pH region of 4 to 6 by the pH control device 14, so that the activity of hydrogen-producing bacteria entrapped and immobilized on the pellets 18 is improved, and hydrogen can be obtained in a high yield.

In addition, according to the above-described embodiment, since the internal of the hydrogen fermenter 12 is maintained at a low pH region of a pH of 4 to 6, the activity of unwanted bacteria that consume the organic matter can be suppressed. The yield of hydrogen can be hereby further improved.

Figure 4:
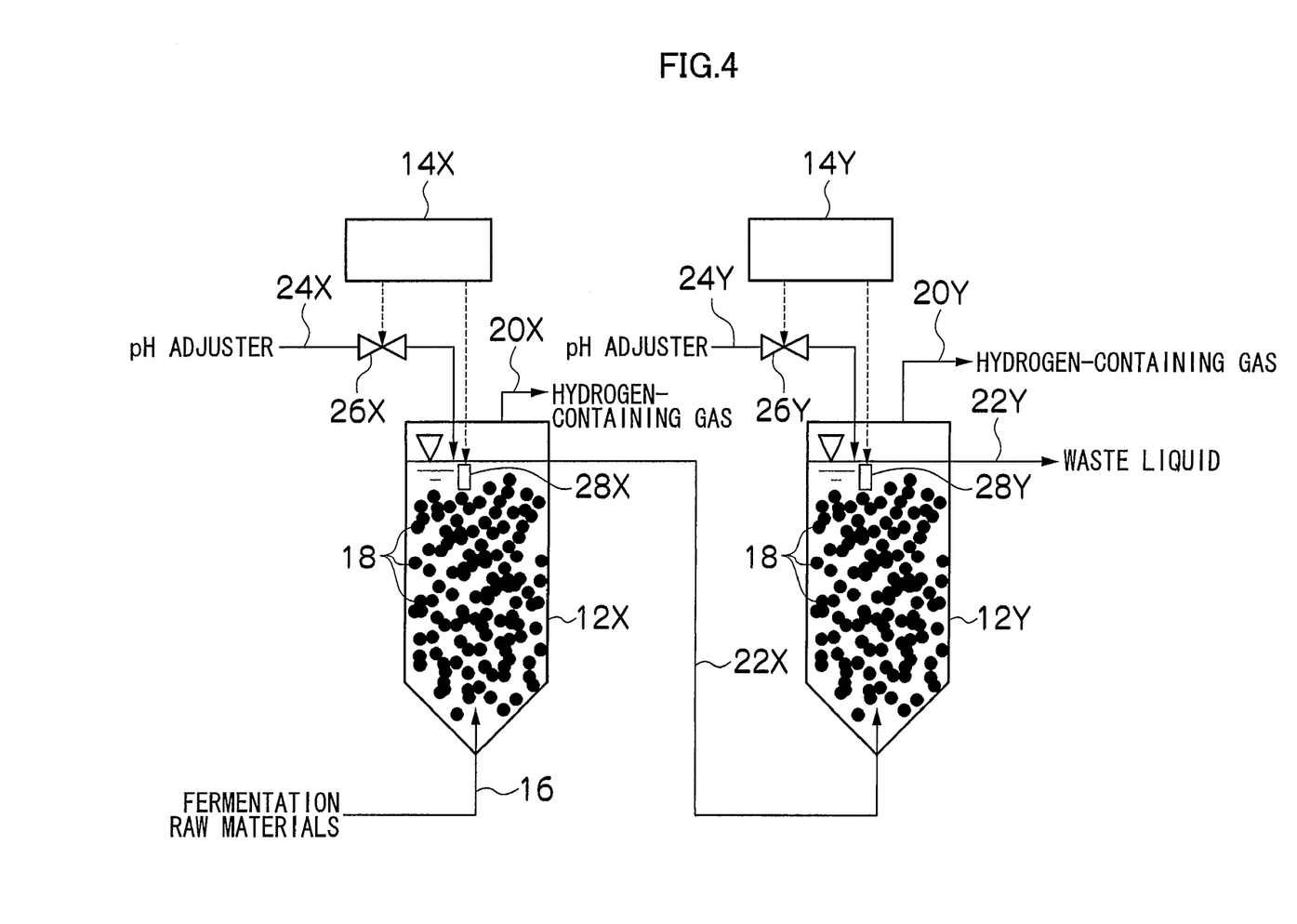
FIG. 4 is a diagram showing a hydrogen-producing apparatus using a two-stage hydrogen fermenter.

FIG. 4 shows a hydrogen-producing apparatus using a two-stage hydrogen fermenter.

In the hydrogen-producing apparatus shown in the figure, the two-stage hydrogen fermenter (hereinafter a first stage tank is referred to as a first hydrogen fermenter 12X, and a second stage tank is referred to as a second hydrogen fermenter 12Y) is provided, and a first hydrogen fermenter 12X and a second hydrogen fermenter 12Y are connected in series. More specifically, a supply pipe 16 supplying fermentation raw materials is connected to the bottom part of the first hydrogen fermenter 12X, and a waste liquid pipe 22X connected to the upper side of the first hydrogen fermenter 12X is connected to the bottom part of the second hydrogen fermenter 12Y. Also, a waste liquid pipe 22Y is connected to the upper side of the second hydrogen fermenter 12Y. Therefore, the fermentation raw materials are supplied to the first hydrogen fermenter 12X via the supply pipe 16, and the hydrogen fermentation is performed within the first hydrogen fermenter 12X. Moreover, a waste liquid from the reaction is supplied to the second hydrogen fermenter 12Y via the waste liquid pipe 22X, and the hydrogen fermentation is performed within the second hydrogen fermenter 12Y. Thereafter, a waste liquid from the reaction is discharged from the waste liquid pipe 22Y.

Incidentally, the first hydrogen fermenter 12X and the second hydrogen fermenter 12Y are charged with the plural pellets 18 on which hydrogen-producing bacteria are entrapped and immobilized. Each of the pellets 18 is contacted with the fermentation raw materials, so that hydrogen is produced within the first hydrogen fermenter 12X and the second hydrogen fermenter 12Y. In addition, a gas pipe 20X and a gas pipe 20Y are connected to the first hydrogen fermenter 12X and the second hydrogen fermenter 12Y respectively, and a hydrogen-containing gas is discharged via the gas pipes 20X and 20Y.

In the first hydrogen fermenter 12X and the second hydrogen fermenter 12Y, a first pH control device 14X and a second pH control device 14Y are provided, respectively. The first pH control device 14X and the second pH control device 14Y are constituted as the pH control device 14 shown in FIG. 3.

More specifically, the first pH control device 14X has an adjuster supply pipe 24X connected to the first hydrogen fermenter 12X, and an on-off valve 26X disposed in the adjuster supply pipe 24X is controlled, so that the pH adjuster is supplied to the first hydrogen fermenter 12X to adjust the pH in the first hydrogen fermenter 12X. Also, the first pH control device 14X is connected to a pH meter 28X provided within the first hydrogen fermenter 12X, and the on-off valve 26X is controlled based on the value measured with the pH meter 28X, thereby controlling the pH in the first hydrogen fermenter 12X to the given pH value. On the other hand, the second pH control device 14Y has an adjuster supply pipe 24Y connected to the second hydrogen fermenter 12Y, and an on-off valve 26Y disposed in the adjuster supply pipe 24Y is controlled, so that the pH adjuster is supplied to the second hydrogen fermenter 12Y to adjust the pH in the second hydrogen fermenter 12Y. Also, the second pH control device 14Y is connected to a pH meter 28Y provided within the second hydrogen fermenter 12Y, and the on-off valve 26Y is controlled based on the value measured with the pH meter 28Y, thereby controlling the pH in the second hydrogen fermenter 12Y to the given pH value.

Incidentally, in the hydrogen-producing apparatus in FIG. 4, the first pH control device 14X and the second pH control device 14Y control the pHs in the hydrogen fermenters to different pH values. In particular, the first pH control device 14X controls the pH in the first hydrogen fermenter 12X to 4 to 5.5, and the second pH control device 14Y controls the pH in the second hydrogen fermenter 12Y to 5.5 or more. The pH in the first hydrogen fermenter 12X is controlled lower than the pH in the second hydrogen fermenter 12Y as described above, so that the growth of contaminated bacteria is suppressed within the first hydrogen fermenter 12X. Also, since the pH in the second hydrogen fermenter 12Y is controlled slightly high, the reaction rate increases. At this time, since the activity of unwanted bacteria is suppressed within the first hydrogen fermenter 12X, the activity of the hydrogen-producing bacteria is more predominant in the second hydrogen fermenter 12Y due to competition between unwanted bacteria and the hydrogen-producing bacteria, so that the yield is further increased. In addition, a pH gradient is provided between the first hydrogen fermenter 12X and the second hydrogen fermenter 12Y, so that a wide range of microflora can be used.

Here, in the above-described embodiments, the one and two-stage hydrogen-producing fermenters are shown, and multi-stage of three and more-stage hydrogen-producing fermenters may be provided. In this case, it is preferred that the pH be controlled to the higher range, as the downstream hydrogen-producing fermenter.

The present hydrogen-producing bacterium is not limited to the above-described examples. More specifically, for example, a mutant strain of PEH8 can be used as the present hydrogen-producing bacterium. As the mutant strain, those inheriting an ability to efficiently produce hydrogen at a low pH range and a high temperature range of PEH8 as described above can be preferably used.

EXAMPLE(S)

(First Test)

As Example 1, the hydrogen fermentation was performed in a hydrogen-producing apparatus 10 in FIG. 3, using an entrapping immobilization hydrogen fermentation pellets on which *Thermoanaerobacterium* strain PEH8 was immobilized. The pellets were prepared as follows. More specifically, cells of *Thermoanaerobacterium* strain PEH8 were suspended in a urethane acrylate prepolymer solution, and potassium persulfate and NNN'N'-tetramethylethylenediamine were added thereto, so that the mixture was subjected to polymerization to give a gel entrapping the bacteria. The amount of each added is as follows.

$7 \times 10^7$ cells/ml solution of *Thermoanaerobacterium* strain PEH8 20%
Urethane acrylate prepolymer 15%
Sterile water 64.25%
NNN'N'-tetramethylethylenediamine 0.5%
Potassium persulfate 0.25%

The gel was formed into 3 mm square to give an entrapping immobilization pellets. A 1-L jar fermenter was charged with the resulting pellets in a volume of 10% and was charged with the medium shown in Table 1 with a retention time of 48 hours, to perform a hydrogen fermentation test in the hydrogen fermenter at a pH of 5.

As Comparative Examples 1 and 2, cells of *Thermoanaerobacterium* strain PEH8 were treated at a state of suspended bacterial cells without being immobilized, to perform hydrogen fermentation at a pH of 5 and a pH of 6 using the same conditions. The result after 1 month of continuous operation is shown in Table 3.

TABLE 3

| | pH in Hydrogen Fermenter | Yield after 1 Month (mol-H$_2$/mol-xylose) |
|---|---|---|
| Example 1 | 5 | 2.2-2.7 |
| Comparative Example 1 | 5 | 0 |
| Comparative Example 2 | 6 | 1.5-2.0 |

As it can be seen from Table 3, the yield in Example 1 applying the present invention was higher than those in Comparative Examples 1 and 2 that are the conventional methods. More specifically, while hydrogen could not be obtained at all in Comparative Example 1 and the yield was as low as 1.5 to 2.0 mol-H$_2$/mol-xylose in Comparative Example 2, the yield was as high as 2.2 to 2.7 mol-H$_2$/mol-xylose in Example 1.
(Second Test)

In the second test, the hydrogen fermentation test was performed using biomass as a raw material.
[Method of Preparing Raw Material]

A method for performing solubilization and glycosylation of lignocellulosic resources such as bagasse (sugarcane trash) includes a method using an acid such as concentrated sulfuric acid or dilute sulfuric acid, a method using alkali such as sodium hydroxide or ammonium, a method using supercritical water, a method using an enzyme, and the like. First, 1.6 kg of bagasse and 16 kg of a 2% (w/w) aqueous sodium hydroxide solution were charged into a 30-L incubator (HMF-30F01, manufactured by Hitachi, Ltd.), and heat-treated in the conditions at 121° C. for 15 minutes. After cooling, solid-liquid separation was carried out with an 80 mesh sieve, and then 18 kg of water was added to 4.5 kg of solid content on the sieve, and the solid was homogenized. The pH of the resulting substance was adjusted to 5.0 with sulfuric acid, and thereafter a commercially available enzyme (GC220: 32 g, MultifectXylanase: 32 g, Genencor International) was added thereto, and the enzyme treatment was carried out in the conditions at 55° C. for 72 hours. Thereafter, 230 g of a yeast extract (PRONAL NS 55 T4, PRODESA) was added thereto, and the mixture was made as a raw material solution. The raw material solution had a composition that a total sugar level by the phenol-sulfuric acid method was 9500 mg/L and the analytical values of reducing sugars by HPLC were 5973 mg/L for glucose, 1776 mg/L for xylose, and 31 mg/L for arabinose.
[Method of Preparing Microorganism Entrapping Immobilization Pellets]

Same as Example 1
[Hydrogen Fermentation]

Figure 5:
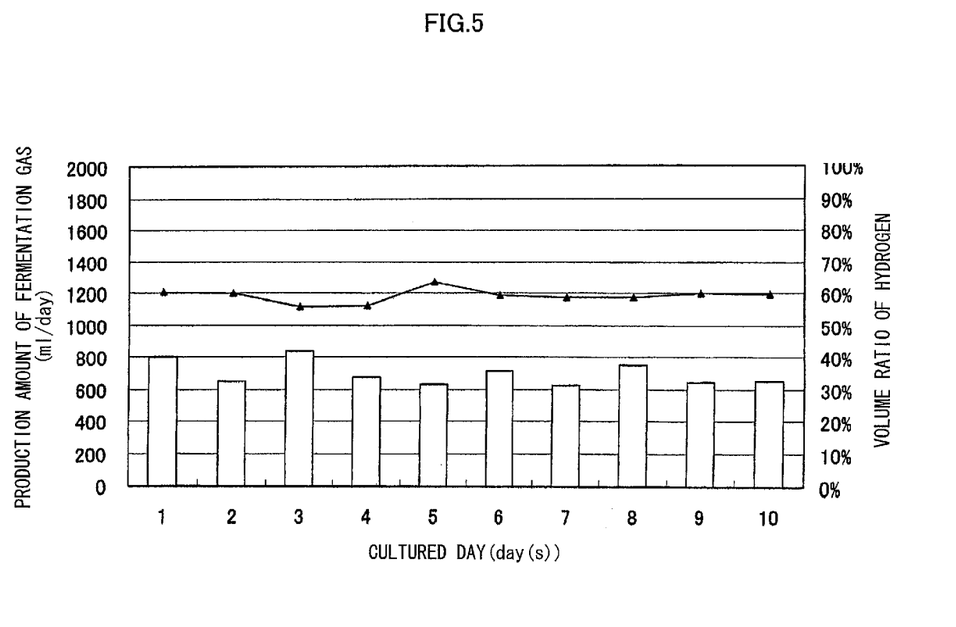
FIG. 5 is a graph showing the results of Examples.

A 1-L jar fermenter (manufactured by ABLE Corporation) was charged with the resulting pellets in a volume of 10% and was charged with the above-described raw material with a retention time of 72 hours, to perform hydrogen fermentation in a hydrogen fermenter at a pH of 5.0. The result of continuous operation from the tenth day to the nineteenth day from the initiation of culture, when biogas generation was stabilized, is shown in FIG. 5. Herein, the culture days (day(s)) 1, and 2 to 10 in the abscissa axis in FIG. 5 shows the tenth day, and the eleventh day to the nineteenth day from the initiation of culture, respectively. Also, the line graph in FIG. 5 shows the volume ratio of hydrogen, and the bar graph in FIG. 5 shows the production amount of fermentation gas (ml/day).

As the average of 10 days, the production amount of fermentation gas was 696 ml/day, and the volume ratio of hydrogen was 59.3%. The yield calculated based on a total sugar level by a phenol-sulfuric acid method was 2.3 mol-H$_2$/mol-sugar (calculated as glucose). It can be seen from the above results that, by using the present inventions, hydrogen can be sufficiently fermented when biomass is used as the raw material.

The invention claimed is:

1. A method for producing hydrogen in which hydrogen is produced from an organic matter using a microorganism, comprising:
    entrapping and immobilizing hydrogen-producing acid-resistant bacteria on pellets;
    contacting and reacting the pellets with the organic matter in an environment of a pH of 4 to 6, thereby producing hydrogen,
    wherein the hydrogen-producing acid resistant bacteria is a strain identified by international deposit accession number FERM BP-10804, which is deposited with the International Patent Organism Depositary, National Institute of Advanced Industrial Science and Technology as Thermoanaerobacterium strain PEH8.

2. The method according to claim 1, wherein the pellets are produced from a prepolymer, wherein the prepolymer is polyethylene glycol diacrylate or polyethylene glycol methacrylate.

3. The method according to claim 1, wherein the produced hydrogen permeates the pellets.

4. The method according to claim 1, wherein the pellets are of a shape selected from the group consisting of globular, cylindrical, rectangular, and string-shaped.

5. The method according to claim 1, wherein the pH is 4.8 to 5.5.

6. The method according to claim 1, wherein the pellets comprise an immobilizing material comprising a network-structure gel, wherein the network-structure gel has a molecular weight of between 2000 to 9000.

7. The method according to claim 1, wherein the pellets and the organic matter are in a first hydrogen fermenter tank and a second hydrogen fermenter tank, wherein said first and second hydrogen tanks are connected in a series for multi-stage fermentation, wherein a pH of said hydrogen tanks is controlled, and wherein the second hydrogen tank has a higher pH range than the pH range of the first hydrogen tank.

* * * * *